US010828641B2

(12) United States Patent
Boehm et al.

(10) Patent No.: US 10,828,641 B2
(45) Date of Patent: Nov. 10, 2020

(54) MICROFLUIDIC DEVICE FOR STORAGE AND WELL-DEFINED ARRANGEMENT OF DROPLETS

(71) Applicant: President and Fellows of Harvard College, Cambridge, MA (US)

(72) Inventors: Christian Boehm, Stuttgart (DE); Amy Rowat, Cambridge, MA (US); Sarah Koester, Bad Urach (DE); Jeremy Agresti, Richmond, CA (US); David A. Weitz, Bolton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 7 days.

(21) Appl. No.: 15/496,750

(22) Filed: Apr. 25, 2017

(65) Prior Publication Data

US 2017/0225167 A1 Aug. 10, 2017

Related U.S. Application Data

(62) Division of application No. 12/990,102, filed as application No. PCT/US2009/002644 on Apr. 28, 2009, now Pat. No. 9,664,619.

(60) Provisional application No. 61/048,304, filed on Apr. 28, 2008.

(51) Int. Cl.
*B01L 3/00* (2006.01)
*B01L 7/00* (2006.01)
*G01N 33/50* (2006.01)
*G01N 21/64* (2006.01)

(52) U.S. Cl.
CPC ........ *B01L 3/502784* (2013.01); *B01L 7/525* (2013.01); *G01N 21/6452* (2013.01); *G01N 33/5008* (2013.01); *B01L 2200/0621* (2013.01); *B01L 2300/087* (2013.01); *B01L 2300/0816* (2013.01); *B01L 2300/0819* (2013.01); *B01L 2300/1827* (2013.01); *B01L 2400/0487* (2013.01); *B01L 2400/086* (2013.01)

(58) Field of Classification Search
None
See application file for complete search history.

(56) References Cited

U.S. PATENT DOCUMENTS

| | | |
|---|---|---|
| 5,460,720 A | 10/1995 | Schneider |
| 5,571,410 A | 11/1996 | Swedberg et al. |
| 5,620,420 A | 4/1997 | Kriesel |
| 5,674,742 A | 10/1997 | Northrup et al. |
| 5,776,674 A | 7/1998 | Ulmer |
| 5,897,838 A | 4/1999 | Kempe |
| 5,950,727 A | 9/1999 | Irani |
| 5,992,820 A | 11/1999 | Fare et al. |
| 6,143,496 A * | 11/2000 | Brown ............... B01L 3/5027 422/504 |
| 6,377,387 B1 | 4/2002 | Duthaler et al. |
| 6,481,453 B1 | 11/2002 | O'Connor et al. |
| 6,557,427 B2 | 5/2003 | Weigl et al. |
| 6,572,830 B1 | 6/2003 | Burdon et al. |
| 6,653,124 B1 | 11/2003 | Freeman |
| 6,653,150 B1 | 11/2003 | Reed |
| 6,673,533 B1 | 1/2004 | Wohlstadter et al. |
| 6,686,084 B2 | 2/2004 | Issacci et al. |
| 6,706,519 B1 | 3/2004 | Kellogg et al. |
| 6,713,298 B2 | 3/2004 | McDevitt |
| 6,716,629 B2 | 4/2004 | Hess et al. |
| 6,737,026 B1 | 5/2004 | Bergh et al. |
| 6,749,814 B1 | 6/2004 | Bergh et al. |
| 6,806,087 B2 | 10/2004 | Kibby et al. |
| 6,863,983 B2 | 3/2005 | Tsapatsis et al. |
| 7,084,240 B2 | 8/2006 | Schaffer et al. |
| 7,312,085 B2 | 12/2007 | Chou et al. |
| 7,556,776 B2 | 7/2009 | Fraden et al. |
| 9,664,619 B2 | 5/2017 | Boehm et al. |
| 2002/0001544 A1 | 1/2002 | Hess et al. |
| 2002/0015149 A1 | 2/2002 | Rahbar-Dehghan |
| 2002/0036018 A1 * | 3/2002 | McNeely ............ B01F 5/0403 137/806 |
| 2002/0058332 A1 | 5/2002 | Quake et al. |

(Continued)

FOREIGN PATENT DOCUMENTS

| | | |
|---|---|---|
| JP | 2005-201707 | 7/2005 |
| WO | WO 96/12541 | 5/1996 |

(Continued)

OTHER PUBLICATIONS

Chaw et al (Lab Chip 7:1041-7) (Year: 2007).*
International Search Report and Written Opinion for International Application No. PCT/US2006/34659 dated Jul. 27, 2007.
International Search Report for International Application No. PCT/US2008/001544 dated Jul. 31, 2008.
International Search Report for International Application No. PCT/US2008/005009 dated Oct. 8, 2008.
International Search Report and Written Opinion for PCT/US2009/002644 dated Dec. 23, 2009.

(Continued)

*Primary Examiner* — Christopher M Gross
(74) *Attorney, Agent, or Firm* — Wolf, Greenfield & Sacks, P.C.

(57) ABSTRACT

The present invention relates to systems and methods for the arrangement of droplets in pre-determined locations. Many applications require the collection of time-resolved data. Examples include the screening of cells based on their growth characteristics or the observation of enzymatic reactions. The present invention provides a tool and related techniques which addresses this need, and which can be used in many other situations. The invention provides, in one aspect, a tool that allows for stable storage and indexing of individual droplets. The invention can interface not only with microfluidic/microscale equipment, but with macroscopic equipment to allow for the easy injection of liquids and extraction of sample droplets, etc.

6 Claims, 8 Drawing Sheets

(56) References Cited

U.S. PATENT DOCUMENTS

| | | |
|---|---|---|
| 2002/0064809 A1* | 5/2002 | Mutz .................. B41J 2/14008 435/40.5 |
| 2002/0068357 A1 | 6/2002 | Mathies et al. |
| 2002/0084185 A1 | 7/2002 | Sundberg et al. |
| 2002/0143437 A1 | 10/2002 | Handique et al. |
| 2002/0170365 A1 | 11/2002 | Sklar et al. |
| 2002/0187564 A1 | 12/2002 | Chow et al. |
| 2003/0039585 A1 | 2/2003 | Freeman |
| 2003/0061687 A1 | 4/2003 | Hansen et al. |
| 2003/0082081 A1 | 5/2003 | Fouillet et al. |
| 2003/0096310 A1 | 5/2003 | Hansen et al. |
| 2003/0102214 A1 | 6/2003 | Munson et al. |
| 2003/0146757 A1 | 8/2003 | Aguero et al. |
| 2003/0148401 A1 | 8/2003 | Agrawal et al. |
| 2003/0173223 A1 | 9/2003 | Gascoyne et al. |
| 2004/0005258 A1 | 1/2004 | Fonash et al. |
| 2004/0005582 A1 | 1/2004 | Shipwash |
| 2004/0028875 A1 | 2/2004 | Van Rijn |
| 2004/0053418 A1 | 3/2004 | Chan et al. |
| 2004/0053422 A1 | 3/2004 | Chan et al. |
| 2004/0072278 A1* | 4/2004 | Chou ................ B01L 3/502761 435/29 |
| 2004/0115830 A1 | 6/2004 | Touzov |
| 2004/0115831 A1 | 6/2004 | Meathrel et al. |
| 2004/0136876 A1 | 7/2004 | Fouillet et al. |
| 2004/0163957 A1 | 8/2004 | Neyer et al. |
| 2004/0171143 A1 | 9/2004 | Chin et al. |
| 2004/0232075 A1 | 11/2004 | Wells |
| 2004/0234966 A1 | 11/2004 | Bryning et al. |
| 2004/0244023 A1 | 12/2004 | Yan et al. |
| 2004/0262223 A1 | 12/2004 | Strook et al. |
| 2005/0002835 A1 | 1/2005 | Shaw et al. |
| 2005/0019794 A1 | 1/2005 | Nassef et al. |
| 2005/0042639 A1 | 2/2005 | Knapp et al. |
| 2005/0062196 A1 | 3/2005 | Hansen et al. |
| 2005/0089863 A1 | 4/2005 | Karlsen et al. |
| 2005/0106066 A1* | 5/2005 | Saltsman .............. B01F 5/0473 422/504 |
| 2005/0205005 A1 | 9/2005 | Hansen et al. |
| 2006/0091085 A1 | 5/2006 | Kobayashi et al. |
| 2006/0231398 A1 | 10/2006 | Sarrut et al. |
| 2007/0003442 A1 | 1/2007 | Link et al. |
| 2007/0003447 A1 | 1/2007 | Gleason et al. |
| 2007/0003448 A1 | 1/2007 | Kanigan et al. |
| 2007/0014695 A1 | 1/2007 | Yue et al. |
| 2008/0003142 A1 | 1/2008 | Link et al. |
| 2009/0130658 A1 | 5/2009 | Barlag et al. |
| 2010/0163109 A1 | 7/2010 | Fraden et al. |
| 2010/0204459 A1 | 8/2010 | Mason et al. |
| 2010/0252118 A1 | 10/2010 | Fraden et al. |

FOREIGN PATENT DOCUMENTS

| | | |
|---|---|---|
| WO | WO 96/39252 | 12/1996 |
| WO | WO 98/00231 | 1/1998 |
| WO | WO 99/64836 | 12/1999 |
| WO | WO 01/34291 | 5/2001 |
| WO | WO 03/037502 | 5/2003 |
| WO | WO 03/055790 | 7/2003 |
| WO | WO 03/068381 | 8/2003 |
| WO | WO 2004/020341 | 8/2003 |
| WO | WO 03/072258 | 9/2003 |
| WO | WO 03/086960 | 10/2003 |
| WO | WO 2004/020590 | 3/2004 |
| WO | WO 2004/034436 | 4/2004 |
| WO | WO 2004/038363 | 5/2004 |
| WO | WO 2004/059299 | 7/2004 |
| WO | WO 2004/076056 | 9/2004 |
| WO | WO 2004/087283 | 10/2004 |
| WO | WO 2004/091763 | 10/2004 |
| WO | WO 2004/103510 | 12/2004 |
| WO | WO 2005/002730 | 1/2005 |
| WO | WO 2005/021151 | 3/2005 |
| WO | WO 2005/118138 | 12/2005 |
| WO | WO 2006/042838 | 3/2006 |
| WO | WO 2006/098696 | 9/2006 |
| WO | WO 2007/118208 | 10/2007 |
| WO | WO 2007/123908 | 11/2007 |

OTHER PUBLICATIONS

Ahn, K., et al., "Electrocoalescence of drops synchronized by size-dependent flow in microfluidic channels," *Applied Physics Letters*, 2006, 88 264105.

Anna, S., et al., "Formation of dispersions using 'flow-focusing' in microchannels," *Applied Physics Letters*, 2003, 82, 364-366.

Avery, S., "Microbial cell individuality and the underlying sources of heterogeneity," *Nat Rev Microbiol*, 2006, 4, 577-587.

Balaban, N., et al., "Bacterial Persistence as a Phenotypic Switch," *Science*, 2004, 305, 1622-1625.

Bishop, A., et al., "Phenotypic heterogeneity can enhance rare-cell survival in 'stress-sensitive' yeast populations," *Mol. Microbiol.*, 2007, 63, 507-520.

Cai, L., et al., "Stochastic protein expression in individual cells at the single molecule level," *Nature*, 2006, 440, 358-362.

Clausell-Tormos, J., et al., "Droplet-Based Microfluidic Platforms for the Encapsulation and Screening of Mammalian Cells and Multicellular Organisms," *Chem Biol*, 2008, 15, 427-437.

Courtois, F., "An Integrated Device for Monitoring Time-Dependent in vitro Expression From Single Genes in Picolitre Droplets," *Chembiochem*, 2008, 9, 439-446.

Duffy, et al. "Rapid Prototyping of Microfluidic System in Poly(dimethylsiloxane)," *Anal. Chem.*, 1998, 70, pp. 4974-4984.

Erdman, S., et al., "Pheromone-regulated Genes Required for Yeast Mating Differentiation," *J Cell Biol*, 1998, 140, 461-483.

Fidalgo, L.M., et al., "From Microdroplets to Microfluidics: Selective Emulsion Separation in Microfluidic Devices," *Angew Chem Int Ed Engl*, 2008, 47, 2042-2045.

Giaever, G., et al., "Functional profiling of the *Saccharomyces cerevisiae* genome," *Nature*, 2002, 418, 387-391.

Gordon, A., et al., "Single-cell quantification of molecules and rates using open-source microscope-based cytometry," *Nat Methods*, 2007, 4, 175-181.

Griffiths, A., et al., "Miniaturizing the laboratory in emulsion droplets," *Trends Biotechnol*, 2006, 24, 395-402.

Hansen, C., et al., "A robust and scalable microfluidic metering method that allows protein crystal growth by free interface diffusion", PNAS, Dec. 2004, vol. 99, No. 26, 16531-16536.

Hansen et al., "Systematic investigation of protein phase behavior with a microfluidic formulator", PNAS, vol. 101, No. 40, pp. 14431-14436, Oct. 5, 2004.

Hansen, C., et al., "A microfluidic device for kinetic optimization of protein crystallization and in situ structure determination," *J Am Chem Soc*, 2006, 128, 3142-3143.

He, M., et al., "Selective Encapsulation of Single Cells and Subcellular Organelles into Picoliter-and Femtoliter-Volume Droplets," *Analytical Chemistry*, 2005, 77, 1539-1544.

Holtze, C., et al., "Biocompatible surfactants for water-in-fluorocarbon emulsions," *Lab on a Chip*, 2008, 8(10), 1632-1639.

Huebner, A., et al., "Development of Quantitative Cell-Based Enzyme Assays in Microdroplets," *Anal Chem*, 2008, 80, 3890-3896.

Huebner, A., et al., "Quantitative detection of protein expression in single cells using droplet microfluidics," *Chem Commun*, 2007, 1218-1220.

Inglese, J., et al., "High-throughput screening assays for the identification of chemical probes," *Nat Chem Biol*, 2007, 3, 466-479.

Kaufmann, B., et al. "Stochastic gene expression: from single molecules to the proteome," *Curr Opin Genet Dev*, 2007, 17, 107-112.

Kelly, B., et al., "Miniaturizing chemistry and biology in microdroplets," *Chem Commun*, 2007, 1773-1788.

Keng et al., Use of flow cytometry in the measurement of cell mitotic cycle. Int J Cell Cloning. Jul. 24, 1986;4:295-311.

Koster et al. "Drop-based microfluidic devices for encapsulation of single cells" *Lab Chip*, 2008, 8, pp. 1110-1115.

(56) References Cited

OTHER PUBLICATIONS

Li, L., et al., "Nanoliter microfluidic hybrid method for simultaneous screening and optimization validated with crystallization of membrane proteins ," *PNAS*, 2006, 103, 19243-19248.

Longo, D., et al, "Dynamics of single-cell gene expression," *Mol Syst Biol*, 2006, 2, 64.

Love, J., et al., "A microengraving method for rapid selection of single cells producing antigen-specific antibodies," *Nat Biotechnol*, 2006, 24, 703-707.

Maerkl, S., et al., "A Systems Approach to Measuring the Binding Energy Landscapes of Transcription Factors," *Science*, 2007, 315, 233-237.

Marcy, Y., et al., "Nanoliter Reactors Improve Multiple Displacement Amplification of Genomes from Single Cells," *PLoS Genet*, 2007, 3, e155, pp. 1702-1708.

Marcy, Y., et al., "Dissecting biological 'dark matter' with single-cell genetic analysis of rare and uncultivated TM7 microbes from the human mouth," *Proc Natl Acad Sci U S A*, 2007, 104, 11889-11894.

McDonald, J., et al., "Poly(dimethylsiloxane) as a Material for Fabricating Microfluidic Devices," *Acc Chem Res*, 2002, 35, 491-499.

Merkel, T., et al., "Gas sorption, diffusion, and permeation in poly(dimethylsiloxane)," *Journal of Polymer Science: Part B: Polymer Physics*, 2000, 38, 415-434.

Ohnuma et al., Sorting of cells of the same size, shape, and cell cycle stage for a single cell level assay without staining. *BMC Cell Biol*. Jun. 22, 2006;7:25.

Prakash, A., et al., "Small volume PCR in PDMS biochips with integrated fluid control and vapour barrier," *Sensors & Actuators: B. Chemical*, 2006, 113, 398-409.

Randall, G., et al., "Permeation-driven flow in poly(dimethylsiloxane) microfluidic devices," *PNAS*, 2005, 102, 10813-10818.

Raser, J., et al., "Noise in Gene Expression: Origins, Consequences, and Control," *Science*, 2005, 309, 2010-2013.

Rowat, A. "Tracking single cell lineages and growth using microfluidic tools," Slides presented at "Boston Area Yeast Meeting," Nov. 29, 2007.

Schmitz et al. "Dropspots: a picoliter array in a microfluidic device," *Lab Chip*, 2009, 9, pp. 44-49.

Shim et al. "Control and Measurement of the Phase Behavior of Aqueous Solutions Using Microfluidics," *J. Am. Chem. Soc.* 2007, 129, pp. 8825-8835.

Song, H., et al., "Reactions in Droplets in Microfluidic Channels," *Angew Chem Int Ed Engl*, 2006, 45, 7336-7356.

St. Onge, R., et al., "Systematic pathway analysis using high-resolution fitness profiling of combinatorial gene deletions," *Nat Genet*, 2007, 39, 199-206.

Suzuki, Y., et al., "Systematic genetics swims forward elegantly," *Mol Syst Biol*, 2006, 2, 48.

Thorsen, T., et al., "Microfluidic Large-Scale Integration," *Science*, 2002, 298, 580-584.

Toussaint, G., et al., "A high-throughput method to measure the sensitivity of yeast cells to genotoxic agents in liquid cultures," *Mutat Res*, 2006, 606, 92-105.

Toussaint, M., et al., "High-throughput and sensitive assay to measure yeast cell growth: a bench protocol for testing genotoxic agents," *Nat Protoc*, 2006, 1, 1922-1928.

Unger, M., et al., "Monolithic microfabricated valves and pumps by multilayer soft lithography," *Science*, 2000, 288, 113-116.

Verneuil, E., et al., "Permeation-induced flows: Consequences for silicone-based microfluidics," *Europhys. Lett.*, 2004, 68, 412-418.

Zheng, B., et al., "A Droplet-Based, Composite PDMS/Glass Capillary Microfluidic System for Evaluating Protein Crystallization Conditions by Microbatch and Vapor-Diffusion Methods with On-Chip X-Ray Diffraction", Angew. Chem. Int. Ed. 2004, 43, 2508-2511.

\* cited by examiner

MICROFLUIDIC DEVICE FOR STORAGE AND WELL-DEFINED ARRANGEMENT OF DROPLETS

RELATED APPLICATIONS

This application is a divisional of U.S. patent application Ser. No. 12/990,102, with a § 371 date of Mar. 16, 2011, entitled "Microfluidic Device For Storage and Well-Defined Arrangement of Droplets," which is a national stage filing of Int. Patent Application Serial No. PCT/US2009/002644, filed Apr. 28, 2009, which claims the benefit of U.S. Provisional Patent Application Ser. No. 61/048,304, filed Apr. 28, 2008, entitled "Microfluidic Device for Storage and Well-Defined Arrangement of Droplets," by Weitz, et al., each of which is incorporated herein by reference in its entirety.

FIELD OF INVENTION

The present invention relates generally to systems and methods for the arrangement of droplets in pre-determined locations.

BACKGROUND

Droplet-based microfluidics is a powerful emerging set of techniques with a great deal of application in chemistry and biology. Droplets can be merged with other droplets, split into multiple droplets, sorted, and/or used to house reactions for example. Droplet-based microfluidic techniques allow for the production and handling of a very high volume of droplets per unit of time. Hence, droplet-based microfluidic devices are an ideal tool for high-throughput applications.

A number of patent applications describe formation and/or use of droplets for these and other procedures. A representative list includes: U.S. patent application Ser. No. 11/246,911, filed Oct. 7, 2005, entitled "Formation and Control of Fluidic Species," published as U.S. Patent Application Publication No. 2006/0163385 on Jul. 27, 2006; U.S. patent application Ser. No. 11/024,228, filed Dec. 28, 2004, entitled "Method and Apparatus for Fluid Dispersion," published as U.S. Patent Application Publication No. 2005/0172476 on Aug. 11, 2005; U.S. patent application Ser. No. 11/360,845, filed Feb. 23, 2006, entitled "Electronic Control of Fluidic Species," published as U.S. Patent Application Publication No. 2007/0003442 on Jan. 4, 2007; International Patent Application No. PCT/US2006/007772, filed Mar. 3, 2006, entitled "Method and Apparatus for Forming Multiple Emulsions," published as WO 2006/096571 on Sep. 14, 2006; U.S. patent application Ser. No. 11/221,585, filed Sep. 8, 2005, entitled "Microfluidic Manipulation of Fluids and Reactions," published as U.S. Patent Application Publication No. 2007/0052781 on Mar. 8, 2007; U.S. patent application Ser. No. 11/698,298, filed Jan. 24, 2007, entitled "Fluidic Droplet Coalescence," published as U.S. Patent Application Publication No. 2007/0195127 on Aug. 23, 2007; and U.S. Provisional Patent Application Ser. No. 60/920,574, filed Mar. 28, 2007, entitled "Multiple Emulsions and Techniques for Formation," each incorporated herein by reference.

Although many advances associated with formation and use of droplets have been achieved, there is a need for improved techniques and tools.

SUMMARY OF THE INVENTION

The present invention relates generally to systems and methods for the arrangement of droplets in pre-determined locations. The subject matter of the present invention involves, in some cases, interrelated products, alternative solutions to a particular problem, and/or a plurality of different uses of one or more systems and/or articles.

In one aspect, the invention is directed to a method or arranging droplets at predetermined positions. In a first set of embodiments, the method comprises urging a first droplet through a first constriction in a channel into a first pot. In some cases, the method further comprises applying a pressure differential along the channel such that the first droplet is urged through a second constriction into a second pot that is downstream of the first pot. In some instances, the method further comprises applying a pressure differential along the channel such that a second droplet is urged through the first constriction into the first pot wherein upon removal of the applied pressure differential, the first droplet is contained within the second pot and the second droplet is contained within the first pot simultaneously.

In another set of embodiments, the method comprises applying a pressure differential along a channel that does not branch such that a first droplet is urged through the channel into a first pot. In some cases, the method further comprises applying a pressure differential such that the first droplet is passed through the channel that does not branch into a second pot that is downstream of the first pot. In additional cases, the method further comprises applying a pressure differential such that a second droplet is passed through the channel that does not branch into the first pot wherein the first droplet is contained within the second pot and the second droplet is contained within the first pot simultaneously.

In another set of embodiments, the method comprises applying a pressure differential in one direction such that a first droplet is urged through a first constriction into a first pot and subsequently urged through a second constriction from the first pot into a second pot. In some cases, the method further comprises applying a pressure differential in one direction such that a second droplet is passed through the channel into the first pot wherein the first droplet is contained within the second pot and the second droplet is contained within the first pot simultaneously.

In another set of embodiments, the method comprises applying an essentially constant pressure gradient along a channel such that a first droplet is urged through a first constriction into a first pot and then urged through a second constriction from the first pot into a second pot. In some cases, the method further comprises continuing to apply the essentially constant pressure gradient such that a second droplet is urged through the first constriction into the first pot wherein the first droplet is contained within the second pot and the second droplet is contained within the first pot simultaneously.

In another set of embodiments, the method comprises applying a pressure differential along a channel comprising a series of pots each containing at least one droplet, said pots connected via a series of constrictions arranged such that each pot is in direct fluid communication with no more than two other pots and each pot is connected to exactly two constrictions, and ejecting the droplets from the exit of the channel in the order in which they were placed in the pots.

In another set of embodiments, the method comprises urging a first cell through a first constriction in a channel into a first pot. In some cases, the method further comprises applying a pressure differential along the channel such that the first cell is urged through a second constriction into a second pot that is downstream of the first pot. In some instances, the method further comprises applying a pressure differential along the channel such that a second cell is urged through the first constriction into the first pot wherein, upon removal of the applied pressure differential, the first cell is contained within the second pot and the second cell is contained within the first pot simultaneously.

In another aspect, the invention is directed to a method of fabricating a device for arranging droplets. In one set of embodiments, the method comprises using a single lithography step to construct a channel comprising a series of pots connected via a series of constrictions arranged such that each pot is in direct fluid communication with no more than two other pots and each pot is connected to exactly two constrictions.

In some embodiments, the method comprises urging a plurality of droplets toward a channel comprising a plurality of pots, wherein at least about 1% of the droplets are immobilized within pots. The method may further comprise, in some embodiments, loading droplets into pots at a rate of at least about 10 droplets per second.

In another aspect, the invention is directed to a device for arranging droplets. In one set of embodiments, the device comprises a channel comprising a series of pots connected via a series of constrictions arranged such that each pot is in direct fluid communication with no more than two other pots and each pot is connected to exactly two constrictions.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
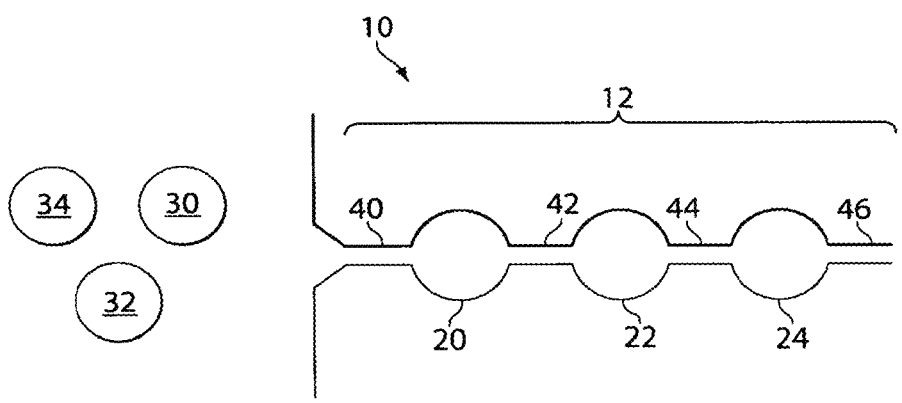
FIG. 1 is a schematic illustrating of an article including an array of pots according to one embodiment of the invention.

The present invention relates to systems and methods for the arrangement of droplets in pre-determined locations. Many applications require the collection of time-resolved data. Examples include the screening of cells based on their growth characteristics or the observation of enzymatic reactions. The present invention provides tools and related techniques which address this need, and which can be used in many other situations. The invention provides, in one aspect, a tool that allows for stable storage and indexing of individual droplets. The invention can interface not only with microfluidic/microscale equipment, but with macroscopic equipment to allow for the easy injection of liquids and extraction of sample droplets, etc.

In one aspect, an inventive device has been fabricated that includes one or more "pots" into which individual droplets can be transported and stored. Another aspect includes methods for arranging droplets in pots. In one embodiment, a droplet is urged through a constriction in a storage channel into a pot. Once in the pot, the droplet may remain stably positioned, or it may be urged from the pot through a second constriction and/or through further constrictions into and/or through various pots which can identical or similar to, or different from, the original pot.

The systems and methods of the invention can be used in a variety of applications that can benefit from the ability to immobilize droplets. For example, nanoliter-scale pots may allow for the observation of many, e.g., thousands, of chemical reactions on a single microfabricated chip where, for example, individual reactions are contained within individual pots (within droplets within those pots) associated with a chip. In some instances, cells can be contained within a droplet, and the cells can be stored and/or delivered and, within pots, reactions involving cells can be carried out and/or observed and/or other cellular interactions (e.g., production of products from cells) can be carried out and/or observed. In some embodiments, the cells themselves may constitute droplets, and the cells may be stored within and/or delivered to pots fluid. Other species that can be stored and/or delivered include, for example, biochemical species such as nucleic acids such as siRNA, RNAi and DNA, proteins, peptides, or enzymes. Additional species that can be incorporated within a droplet of the invention include, but are not limited to, nanoparticles, quantum dots, indicators, dyes, fluorescent species, chemicals, or the like. Droplets can also serve as reaction vessels in certain cases, such as for controlling chemical reactions, or for in vitro transcription and translation, e.g., for directed evolution technology.

Embodiments are described generally herein with reference to a set of fluidic droplets, carried in a second fluid, and urged through constrictions into pots in which they can reside in the absence of another urging force or below a threshold force. In all embodiments herein it is to be understood that droplets of a first fluid, carried in a second, continuous fluid can be replaced by other conformable objects such as cells (described in greater detail herein) which can, but need not be, carried in a carrier liquid. For example, cells or other conformable objects can be arranged in pots of the invention surrounded by another fluidic substance, a gas, or the like. Examples of conformable substances include cells, gels, deformable polymers, and of the like.

FIG. 1 is a schematic of a device 10 according to one embodiment of the invention. The illustrative embodiment includes a storage channel 12, e.g., an essentially straight storage channel, comprising a series of pots (20, 22, and 24) and constrictions (40, 42, 44, and 46). As used herein, the term "pot" refers to a portion of a storage channel with a maximum cross-sectional area that is larger than the maximum cross-sectional area of a portion or portions of the storage channel directly adjacent to the pot. In some embodiments, pots are spherical in shape with the exception, of course, of portions of the essentially spherical pot defining inlets and/or outlets (e.g., constrictions as shown in FIG. 1). In some embodiments, pots may be other shapes including cylinders, cubes, and cuboids, among others. Devices described herein may include any number of pots. In some cases, a device comprises a single pot. In other instances, a device may comprise at least 100, at least 1000, or at least 10,000 pots. In addition, the pots described herein may be of any volume. In some cases, the volumes of one or more pots are less than about 100 femtoliters, less than about 500 femtoliters, less than about 5 picoliters, less than about 100 picoliters, less than about 500 picoliters, less than about 1 nanoliter, or less than about 10 nanoliters.

Pots may be used to store droplets (30, 32, 34). The term "droplet," as used herein, refers to an isolated portion of a first fluid that is surrounded by a second fluid, where the first and second fluids are immiscible on the time scale of use of the device of the invention. As used herein, the term "fluid" generally refers to a substance that tends to flow and to conform to the outline of its container. Typically, fluids are materials that are unable to withstand a static shear stress, and when a shear stress is applied, the fluid experiences a continuing and permanent distortion. The fluid may have any suitable viscosity that permits at least some flow of the fluid. Non-limiting examples of fluids include liquids and gases, but may also include free-flowing solid particles (e.g., cells, vesicles, etc.), viscoelastic fluids, and the like. Making and using such droplets, including use in a variety of chemical, biological or biochemical settings, are described in various documents including U.S. patent application Ser. No. 11/643,151, filed Dec. 20, 2006, entitled "Compartmentalised combinatorial chemistry by microfluidic control," published as U.S. Patent Application Publication No. 2007/0184489 on Aug. 9, 2007 and in International Patent Application No. PCT/US2006/007772, filed Mar. 3, 2006, entitled "Method and Apparatus for Forming Multiple Emulsions," published as WO 2006/096571 on Sep. 14, 2006, incorporated herein by reference. In some preferred embodiments, the droplet(s) are spherical. In some embodiments, the droplet(s) are not necessarily spherical, but may assume other shapes as well, for example, depending on the external environment (e.g., a shape of a pot within which a droplet is contained; typically, when a droplet is passed through a constriction defining an inlet to a pot, it assumes a shape different than that which it assumes within the pot). In one embodiment, a droplet will have a maximum cross-sectional dimension that is larger than the smallest dimension of a constriction perpendicular to fluid flow in which the droplet is located. When a population of droplets is used, the droplet(s) in such an arrangement will have an average cross-sectional dimension that is larger than the smallest dimension of a constriction perpendicular to fluid flow in which the droplet is located. In this context, the cross-sectional dimension of a droplet is such a dimension when the droplet is not physically constrained by, for example, a constriction or inlet to a pot, but one in which the droplet's shape is controlled by the free energy of the droplet and its surrounding environment. As mentioned above, the droplet(s) may contain additional entities or species which may be any substance that can be contained in any portion of a droplet and can be differentiated from the droplet fluid.

In cases where multiple droplets are present, the droplets may each be substantially the same shape and/or size ("monodisperse"). The shape and/or size of the droplets can be determined, for example, by measuring the average diameter or other characteristic dimension of the droplets. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, at least about 20 micrometers, or at least about 100 micrometers in certain cases.

As noted, in the illustrative embodiment are a series of constrictions (40, 42, 44, and 46 in FIG. 1). As used herein, the term "constriction" refers to a portion of a storage channel with a cross-sectional area that is smaller than those of the portions of the storage channel directly adjacent to the constriction, e.g., pots. In order to promote confining the droplets to pots, the minimum cross-sectional diameters of the constrictions may be smaller than the maximum cross-sectional diameters of the adjacent pots. In some embodiments, the minimum cross-sectional diameters of the constrictions are less than 50% of the maximum cross-sectional diameters of the adjacent pots. In some embodiments, the minimum cross-sectional diameters of the constrictions are less than 25%, less than 10%, or less than 5% of the maximum cross-sectional diameters of the adjacent pots.

While description of the relationship between pots, constrictions, and droplets is provided, it should be understood that in one embodiment all pots of a single storage channel, or all pots of an entire device, are of the same size, with all constrictions of a single storage channel or of an entire device being the same size, and all droplets are essentially the same size, but in other arrangements different pot sizes, different constriction sizes and/or different droplets can be used. Those of ordinary skill in the art will understand that such variability can occur for a variety of purposes, and will understand that wherever single sizes of any of the above are described multiple sizes can be selected. Additionally, any number of pots can be used in a single storage channel, and any number of storage channels can be used, in series or parallel, in a particular device.

The devices described herein comprise, in one set of embodiments, one or more storage channels. A "storage channel," as used herein, means a feature on or in an article (substrate) that at least partially directs flow of a fluid and comprises one or more pots connected via a series of at least two constrictions. The channel can have any cross-sectional shape (circular, oval, triangular, irregular, square or rectangular, or the like) and can be enclosed or unenclosed. In embodiments where it is completely enclosed, at least one portion of the channel can have a cross-section that is completely enclosed, or the entire channel may be completely enclosed along its entire length with the exception of its inlet(s) and/or outlet(s). A channel may also have an aspect ratio (length to average cross sectional dimension) of at least 2:1, more typically at least 3:1, 5:1, 10:1, 50:1, 100:1 or more. An unenclosed channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an unenclosed channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. The dimensions of the channel may also be chosen, for example, to allow a certain volumetric or linear flowrate of fluid through the channel. Of course, the number of channels and the shape of the channels can be varied by any method known to those of ordinary skill in the art.

In some embodiments, including that shown in FIG. 1, the pots and constrictions in the storage channel are arranged such that each pot is in direct fluid communication with no more than two other pots, and each pot is connected to exactly two constrictions. In some embodiments, the storage channels comprising pots and constrictions do not branch. In some cases, the storage channels do not branch between the first and last pots in the storage channel. The term "branch," as used herein, means to divide or separate into two or more parts or subdivisions. The storage channels of the device may, in some instances, be substantially straight. In some embodiments, the storage channels may be serpentine, circular, or follow any other type of path.

A variety of materials and methods, according to certain aspects of the invention, can be used to form systems described herein. In some cases, the various materials selected lend themselves to various methods. For example, various components of the invention can be formed from solid materials, in which the storage channels can be formed via micromachining, film deposition processes such as spin coating and chemical vapor deposition, laser fabrication, photolithographic techniques, etching methods including wet chemical or plasma processes, and the like. See, for example, *Scientific American,* 248:44-55, 1983 (Angell, et al). In one set of embodiments, a single lithography step may be used to construct the devices described herein. In one embodiment, the devices and/or molds used to produce the devices described herein may be microfabricated using a single bulk etching step. For example, in one set of embodiments laser etching could be used to make devices in a one-step process. As another example, in one set of embodiments a master may be fabricated using standard photolithography. The structure on the master may be essentially the same height everywhere. The master may be molded in PDMS. In this case, since the resulting channels would have essentially the same height throughout the device, several layers of photoresist and/or several layers of PDMS would not be needed. In one embodiment, at least a portion of the fluidic system is formed of silicon by etching features in a silicon chip. Technologies for precise and efficient fabrication of various fluidic systems and devices of the invention from silicon are known. In another embodiment, various components of the systems and devices of the invention can be formed of a polymer, for example, an elastomeric polymer such as polydimethylsiloxane ("PDMS"), polytetrafluoroethylene ("PTFE" or Teflon®), or the like.

Different components can be fabricated of different materials. For example, a base portion including a bottom wall and side walls can be fabricated from an opaque material such as silicon, and a top portion can be fabricated from a transparent or at least partially transparent material, such as glass or a transparent and/or partially transparent polymer (e.g., PDMS), for observation and/or control of the fluidic process. Components can be coated so as to expose a desired chemical functionality to fluids that contact interior storage channel walls, where the base supporting material does not have a precise, desired functionality. For example, components can be fabricated as illustrated, with interior storage channel walls coated with another material. Material used to fabricate various components of the systems and devices of the invention, e.g., materials used to coat interior walls of fluid storage channels, may desirably be selected from among those materials that will not adversely affect or be affected by fluid flowing through the fluidic system, e.g., material(s) that is chemically inert in the presence of fluids to be used within the device.

In one embodiment, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred in one set of embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric, and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces.

Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," Anal. Chem., 70:474-480, 1998 (Duffy, et al.), incorporated herein by reference.

In some embodiments, certain microfluidic structures of the invention (or interior, fluid-contacting surfaces) may be formed from certain oxidized silicone polymers. Such surfaces may be more hydrophilic than the surface of an elastomeric polymer. Such hydrophilic storage channel surfaces can thus be more easily filled and wetted with aqueous solutions.

In one embodiment, a bottom wall of a microfluidic device of the invention is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, bonding, solvent bonding, ultrasonic welding, etc.

Figure 2A:
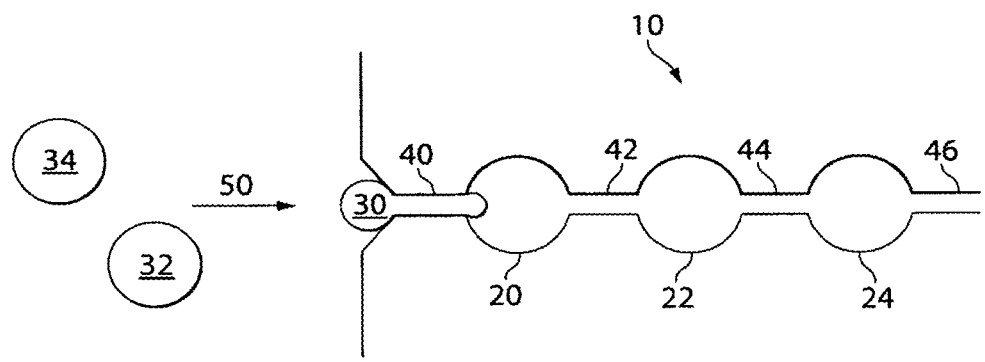
FIGS. 2A-D are schematics illustrating the placement of droplets in pots according to one embodiment of the invention.
Figure 2B:
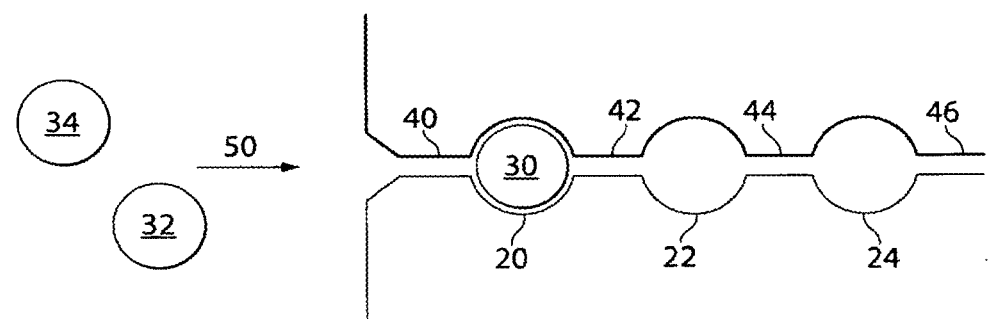
Figure 2C:
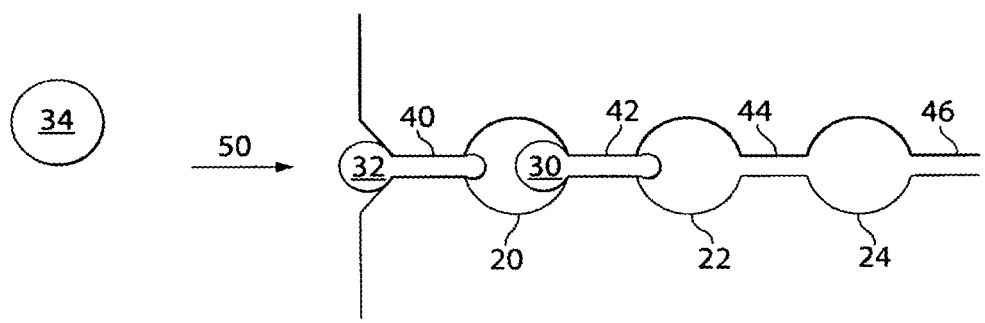
Figure 2D:
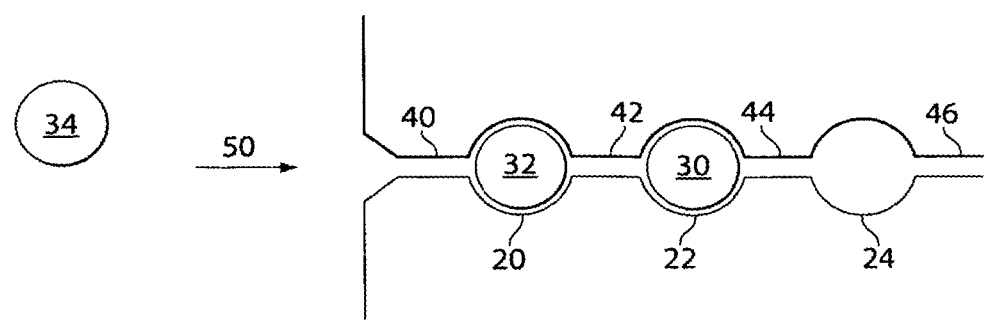

In another aspect, the present invention relates generally to methods for the arrangement of droplets in pre-determined locations. FIGS. 2A-D illustrate a method, according to one embodiment, of arranging droplets in pots. In this embodiment, first droplet 30 is urged through first constriction 40 and into first pot 20. As seen in FIG. 2A, first droplet 30 is deformed as it is urged through constriction 40. The deformation of droplet 30 as illustrated in FIG. 2A may be achieved by applying a pressure gradient across the droplet. A "pressure gradient," as defined herein, describes a situation in a fluid continuum in which a point of relatively high pressure and a point of relatively low pressure exist simultaneously and the points of relatively high and relatively low pressure are on opposite sides of the droplet. Typically, a pressure gradient will exist between the inlet of a storage channel and the outlet of the channel. Pressure gradients in the system may be applied by those methods known in the art such as, for example, through the use of syringe pumps. In some cases, the pressure gradient across the channel may be very accurately controlled using such methods. In the embodiments outlined in FIGS. 2A-D, a pressure gradient is applied such that the pressure decreases in the direction of arrow 50. In FIG. 2B, droplet 30 has entered pot 20 and relaxed to its free energy (in the embodiment illustrated, and essentially spherical) shape. If the pressure gradient is reduced below a critical value or completely eliminated, droplet 30 may remain confined in pot 20. For example, the pressure gradient may be eliminated by simultaneously disconnecting all external tubing (e.g., by pulling it out of the device or cutting it off), thereby exposing all channel openings to the same atmospheric pressure. Alternatively, droplet 30 may be urged through constriction 42, as shown in FIG. 2C. In some embodiments, second droplet 32 may be urged through first constriction 40 as first droplet 30 is simultaneously urged through second constriction 42. Eventually, second droplet 32 will enter first pot 20, and first droplet 30 will enter second pot 22. Both droplets will relax to their natural round shape once they have entered the pots as shown in FIG. 2D.

Figure 3:
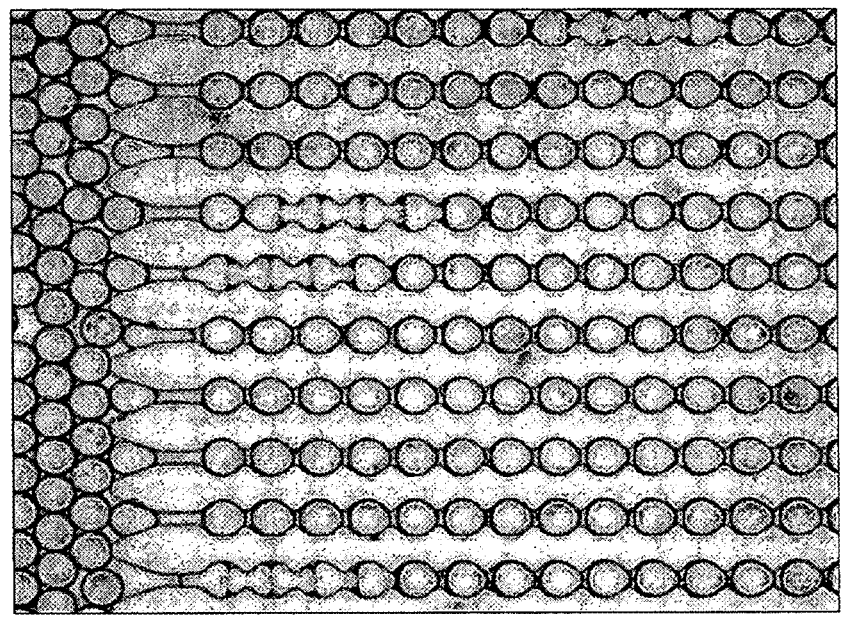
FIG. 3 is an optical micrograph of an article according to one embodiment of the invention.
Figure 4:
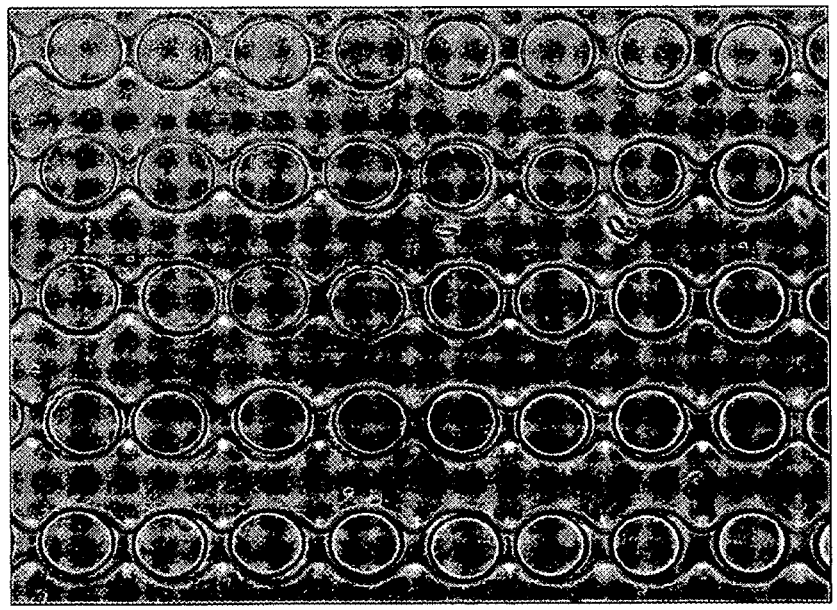
FIG. 4 is an optical micrograph of an article according to one embodiment of the invention.

If the pressure gradient is reduced below a critical value or completely eliminated, the droplets will remain confined in their pots. First droplet 30 may, in some cases, be urged through third constriction 44 into third pot 24, second droplet 32 may be urged through second constriction 42 into second pot 22, and third droplet 34 may be urged through first constriction 40 into first pot 20. This process may be repeated for any number of pots and/or droplets. FIGS. 3-4 include optical micrographs of droplets arranged in an array of pots according to one embodiment.

In some embodiments, the pressure gradient used to urge droplets into pots remains substantially constant in direction, magnitude, or both. As used herein, the phrase "constant pressure gradient" refers to pressure gradient does not change in magnitude or direction with time.

Based on the description herein, those of ordinary skill in the art can readily position a variety of droplets in a variety of pots in a static or dynamic arrangement. That is, using pressure gradients any number of droplets can be positioned in any number of specific pots and then analyzed or used for any of a variety of purposes. Similarly, droplets can be move through storage channels in a controlled manner. For example, a pressure gradient can be selected to move droplets through constrictions into successive pots at a rate at which droplets will remain in post for a length of time sufficient to carry out a particular procedure. That is, at a particular pressure gradient a droplet may pass from one pot through a constriction into a downstream pot but then remain in the downstream pot for a period of time, then be urged through a subsequent constriction into a subsequent pot but similarly remain in the subsequent pot for a particular period of time. In this manner, the pressure gradient can be controlled such that droplets move from pot-to-pot but remain in pots long enough for an analysis, reaction, or other technique to be carried out.

In some embodiments, droplets may be loaded into pots at relatively high efficiencies, which is to say, a relatively large number of droplets that are urged toward a channel comprising pots are immobilized within the pots. A droplet may not be immobilized within a pot for a variety of reasons. For example, the droplet may flow through a bypass channel (an example of which is described in Example 1) rather than through a channel comprising pots. In some cases, a droplet could rupture or merge with another droplet. As another example, a droplet may be leaked out of the device or the loading instrument (e.g., a pipette, syringe, etc.) over the time scale of the loading process. In some embodiments, a plurality of droplets are urged toward a channel comprising a plurality of pots, and at least about 1%, at least about 10%, at least about 25%, at least about 50%, at least about 75%, at least about 90%, at least about 95%, or at least about 99% of the droplets are immobilized within pots. In some embodiments, droplets are produced within a device comprising a storage channel. In such cases, urging the droplets toward a channel comprising a plurality of pots may comprise exerting a pressure on the fluid containing the droplets such that the fluid containing the droplets is flowed into the channel comprising the plurality of pots. In some cases, urging droplets toward a channel comprising a plurality of pots may comprise loading droplets into the device comprising the storage channel via a pipette, syringe, or other external instrument. In such cases, a droplet is said to be urged toward a channel comprising a plurality of pots once the droplet exits the pipette, syringe, or other external container.

Droplets may be urged into pots at a relatively fast rate. For example, in some cases, droplets may be urged into pots at a rate of at least about 10, at least about 100, at least about 1000, or at least about 10,000 droplets per second. Droplets may be urged into pots at high rates (e.g., any of the rates listed above) while maintaining any of the above loading efficiencies, in some embodiments.

In another set of embodiments, a method for removing droplets from pots is described. In some cases, droplets can be removed one at a time, in the order in which the droplets entered the storage channel. This may be achieved, for example, by applying a pressure gradient. The pressure gradient may be constant in direction, magnitude, or both. In some cases, a third fluid may be provided at the exit of the storage channel. Constant volumes of the third fluid may be provided after the exit of a number of droplets, in some instances, in order to maintain constant spacing between droplets or sets of droplets. In some cases, constant volumes of fluid may be provided after each droplet exits the storage channel.

In some cases, the droplets may be removed from the pots and transported to a secondary device for analysis. The method of removing the droplets from pots may, in some embodiments, comprise applying a pressure gradient along the storage channel and urging the droplets through the exit one at a time. In other embodiments, a hole may be formed adjacent to the pot and the contents of the pot may be drained into a secondary device. Examples of secondary devices include, but are not limited to, microtiter plates (96-well, 140-well, 384-well, 1536-well, etc.), DNA microarrays (also known as a gene or genome chip, DNA chip, or gene array), protein arrays, chemostats, fluorescence activated cell sorters (FACS), flow cytometers, microreactors, and microfluidic devices, among others. As one example, holes may be formed adjacent to the pots of one device, and the contents of those pots may be transferred into the wells of a microtiter plate.

The devices and methods described herein may be used, in some embodiments, to grow cells. For example, single cells may be grown in each pot and/or droplet. Multiple cells may also be grown in each pot and/or droplet in some cases. Cell growth may also arise, in some cases, from a single original cell or from two or more original cells. In some cases, multiple cells of different species may be co-encapsulated (e.g., for directed coevolution). In some embodiments, droplets and/or pots may be used to grow multicellular organisms (e.g. *C. elegans*). In some instances, pots and/or droplets may include one or more suspension cells. In some cases, pots and/or droplets may include one or more adherent cells. In some cases, adherent cells are grown on beads within the pot and/or droplet. The devices and methods described herein may be used to determine the property of a droplet and/or its contents. In some embodiments, properties of droplets may be determined while they are confined to pots. In some embodiments, extraneous substances (e.g. drugs) may be flowed through the channels and around the droplets during their confinement. This may be accomplished by flowing the substances at flow rates low enough to prevent deformation of the cells. In other embodiments, properties of droplets may be determined after they have been transferred to a secondary device (e.g., the well of a microtiter plate or a DNA microarray). As a non-limiting example, a microarray scanner may be used to measure the fluorescence of a droplet that resides in a pot. As another example, a camera can be used to record an image of the contents of pots. Properties of droplets that may be determined (in pots, secondary devices, or in some other location) include fluorescence, changes in phase within a droplet (e.g. nucleation, freezing), the level of gene expression, the amount of a chemical secreted by a cell, the amount of a chemical taken up by a cell, the number of positive reactions in an array of droplets, changes in morphology or shape or structure of encapsulated contents (e.g. cells, packing of colloidal particles, etc.), whether a cell is alive or dead, the motion of a cell, the motility of a cell, the reaction of a cell to drug exposure, the phenotype of a cell (e.g., from an image of a cell), the number of cells in a droplet, and the growth rate of cells, among others.

Systems and methods of the current invention may be used to monitor one or more droplets as a function of time. As an example, a device may comprise an array of pots each filled with one droplet. Each droplet remains in one location on the chip, in this case, and the time course of its contents can be monitored, for example, by imaging the sample with a camera. As another example, suspension cells can be immobilized, and their responses may be tracked over time. In some cases, the droplets and/or their contents (e.g., one or more cells) may be kept in the field of view and in the focal plane of an imaging device (e.g., a camera, microscope, etc.) while the droplets and/or cells remain confined in pots. This may be important, for example, in the case of cells that cannot be immobilized without showing changes in their behavior/metabolism. As another example, one may excite fluorescence in the sample (e.g., with a laser, UV lamp, ACR lamp, LED, and/or halide lamp, among others) and monitor the intensity over time. Other instruments may be used to measure one or more properties of the contents of one or more pots including, but not limited to, scanning detectors such as PMTs, confocal microscopy, and spectroscopy among others. In some cases, many droplets can be monitored simultaneously, for example, by using a camera with a wide-angle view or by moving the device relative to the imaging instrument to sequentially image the droplets in different wells. The ability to monitor droplets as a function of time allows the user to calculate properties such as, for example, reaction rates, growth rates, survival, and phenotype, among others. In one embodiment, differences in reaction rates among two or more droplets may be used as the basis to sort those droplets. In another set of embodiments, the time evolution of fluorescence in individual pots and/or droplets containing single cells can be used as part of a digital PCR or real-time PCR analysis. In some cases, monitoring growth of cells in pots and/or droplets allows for fitness or toxicity assays to be performed at the single cell level. In still other cases, single cells and their progeny remain isolated in pots and/or droplets, and microcolonies deriving from single cells can be maintained over time. Cell tracking can also be performed in cases where cell growth originates from multiple cells.

In some embodiments, droplets remain in pots during and/or after a perturbation. In one embodiment, droplets remain in their pots while the device is moved. For example, droplets may remain in their pots while the device is transported or shipped from one lab to another. In some embodiments, droplets may remain in pots while the device is moved from one table to another. In some cases, the devices may be transported to and stored in a drawer or an incubator overnight or for several days. Droplets may also remain in their pots, for example, after the device is dropped on the floor. In some embodiments, droplets are maintained in their pots as the device is heated. In some cases, droplets remain in their pots as the device is heated to a temperature of at least about 50° C. In other cases, droplets remain in their pots as the device is heated to a temperature of at least about 100° C. or at least about 200° C.

In some embodiments, the environment of the device may be controlled. In some cases, the temperature of the device may be controlled, e.g., when performing PCR analysis. The device may be thermally cycled by, for example, placing the device on a hot plate at the desired temperature. In some embodiments, the device may be substantially isothermal. In other cases, heating may be achieved in a localized area by using, for example, resistive heating.

In some cases, one or more of the walls of the device may comprise a selectively permeable material. For example, one or more walls of the device may comprise a water-permeable material. As another example, one or more walls of the device may comprise a gas-permeable material, allowing for gas exchange across the surface. The selectively permeable material may be located between pots, in some embodiments. For example, the placement of permeable material between two or more pots may allow for the exchange of media (e.g., a buffer, etc.) between pots. The selectively permeable material may separate the contents of the pot from a controlled environment in some cases. In some embodiments, the selectively permeable material may separate the contents of the pot from the ambient atmosphere. The device may also be easily moved to an incubator. In some cases, the use of a selectively permeable material may lead to the unwanted evaporation of liquid (e.g., water) from the device. The evaporative effect may be minimized, in some cases, by sealing the device (e.g., with a glass slide) and saturating the selectively permeable material with liquid (e.g., water) to prevent evaporation. In some embodiments, the evaporation of liquid may be desirable. For example, the evaporation of liquid from the device channels may lead to changes in concentrations in the droplets. In some cases, the evaporation of the liquid from the device channel can be controlled, leading to controlled concentration variation within the droplets. This technique may be useful in applications such as, for example, protein crystallization.

In one set of embodiments, the droplets may contain cells or other entities, such as proteins, viruses, macromolecules, particles, etc. Cells may also constitute droplets in some embodiments. As used herein, a "cell" is given its ordinary meaning as used in biology. One or more cells and/or one or more cell types can be contained in a droplet. Cells, for example, can be suspended in a fluid such as, for example, an aqueous buffer solution or contained in a polymerosome. If a polymerosome is used, the shell surrounding the cell may be formed of a material capable of protecting the cell. The shell may help retain, for example, moisture, and can be sized appropriately to maximize the lifetime of the cell within the polymerosome.

The cell may be any cell or cell type. For example, the cell may be a bacterium or other single-cell organism, a plant cell, or an animal cell. The cell may be, in some cases an adherent cell and, in other cases, a suspension cell. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. If the cell is from a multicellular organism, the cell may be from any part of the organism. For instance, if the cell is from an animal, the cell may be a cardiac cell, a fibroblast, a keratinocyte, a heptaocyte, a chondracyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some cases, the cell may be a genetically engineered cell. In certain embodiments, the cell may be a Chinese hamster ovarian ("CHO") cell or a 3T3 cell. In some cases, multicellular organisms (e.g. C. elegans) may be used in the embodiments described herein.

As used herein, the term "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The average diameter of a single droplet, in the case of a non-spherical droplet, is the diameter of a perfect sphere having the same volume as the non-spherical droplet.

As used herein, two fluids are "immiscible," or not miscible, with each other when one is not soluble in the other to a level of at least 10% by weight at the temperature and under the conditions at which the multiple emulsion is produced. For instance, two fluids may be selected to be immiscible within the time frame of a particular technique carried out in accordance with the invention.

The term "determining," as used herein, generally refers to the analysis or measurement of a species, for example, quantitatively or qualitatively, and/or the detection of the presence or absence of the species. "Determining" may also refer to the analysis or measurement of an interaction between two or more species, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasielectric light scattering; polarimetry; refractometry; or turbidity measurements.

The following examples are intended to illustrate certain embodiments of the present invention, but do not exemplify the full scope of the invention.

Example 1

Figure 6:
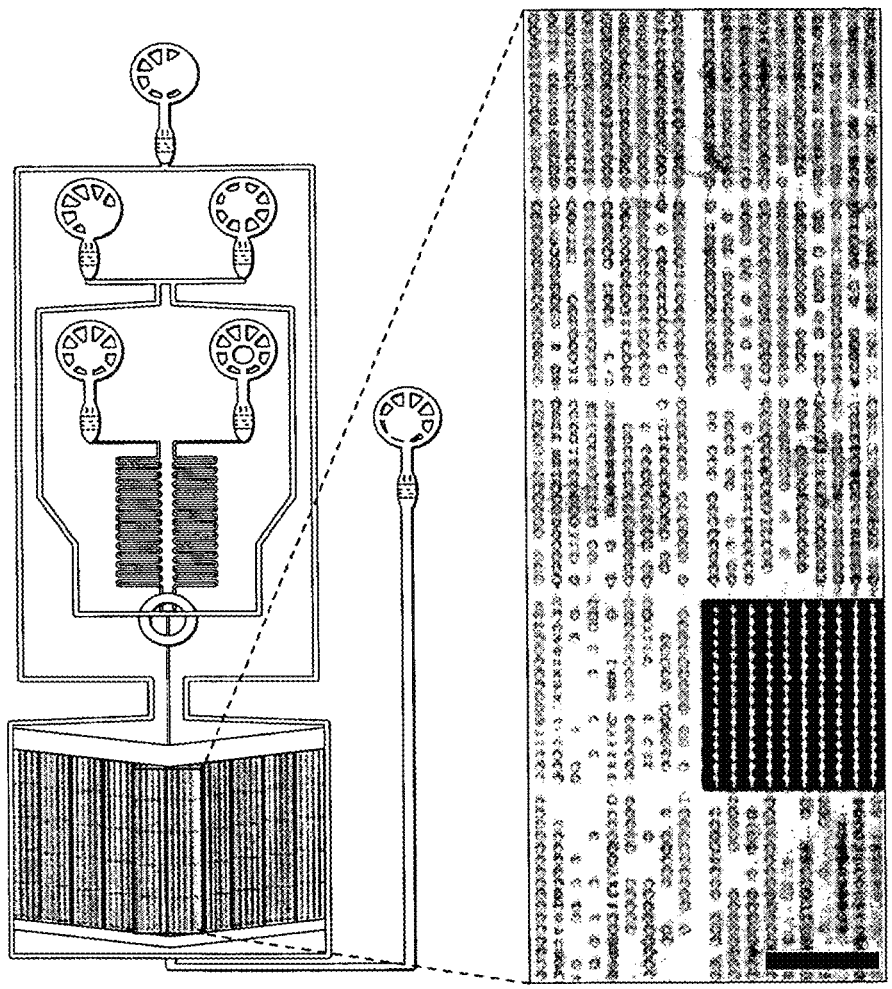
FIG. 6 includes an illustration of an article including an array of pots according to one embodiment of the invention.

This example describes a device used to arrange droplets in predetermined locations. FIGS. 3 and 6 are optical micrographs of articles according to one embodiment of the invention. In this case, the pots comprise cylindrical chambers. The pots are arranged in a series of straight channels, with each pot in fluidic communication with exactly two constrictions.

The device in this example is fabricated by forming the features in PDMS using a mold. Soft lithography was used to fabricate microfluidic channels in polydimethylsiloxane (PDMS, Sylgard 184 Silicone Elastomer, Dow Corning, Midland, Mich., USA). The desired design was printed onto a transparency with features no smaller than 10 μm (CAD/Art Services, Inc., Bandon, Oreg.). SU8-2025 (Microchem, Newton, Mass., USA) was spincoated onto a cleaned silicon wafer to a final thickness of 25 μm following the protocol described by the manufacturer. Exposure to UV light (200-250 mJ, OAI, San Jose, Calif.) crosslinked the exposed pattern, and the non-exposed photoresist is dissolved away using propylene glycol monomethyl ether acetate (PG-MEA). Degassed PDMS with 10% (w/w) crosslinking agent was then poured onto the SU8-mold. After heating at 65° C. for 1 hour, the structure was carefully peeled off the mold, plasma-treated, and bonded to a 1×3" glass slide (1.2 mm thickness). Holes connecting to the channels were formed using biopsy punches (Harris Uni-Core, 0.75 mm diameter). Polyethylene tubing (PE-20, VWR) was inserted into the holes. Before use, channels were treated with Aquapel (The Tire Rack, South Bend, Ind.) followed by a flush with air. This treatment ensured that the oil carrier phase, and not the aqueous phase, wetted the surface.

During prolonged droplet storage, the absorbance of water by PDMS may cause droplets to shrink. To counter this problem, small glass coverslips were placed directly above the storage areas of the device by submerging them in the liquid PDMS before curing. This served to reduce the volume of PDMS in direct contact with the storage channels. Additionally, water channel surrounding the entire storage area of the Dropspots device was fabricated. The water in the channel saturated the surrounding PDMS and prevented evaporation of water from the device. In this case, essentially constant humidity was maintained in the pots, thus preventing the droplets from shrinking when stored in the device. No observable shrinkage was observed, even when droplets were stored for days.

In this embodiment, droplets were formed at rates of 1-10 kHz using a nozzle (not shown) in the area to the left of the image. Droplets were flowed into the channels and squeezed through the constrictions in the presence of flow. When fluid flow was stopped, droplets stopped in the pots. In some cases, single cells were placed in the droplets by tuning the density of the cell suspension such that 1 or 0 cells were placed in each droplet.

In some cases, a bypass channel was incorporated into the device. In these cases, droplets can flow either into the array of pots or the bypass channel. This configuration allowed for the adjustment of the flow speed of the droplets as they entered the storage array. In this example, flow speed was adjusted by manually controlling the pressure applied to the bypass channel inlet. In this way, the proportion of droplets entering the bypass channel (e.g., waste) was controlled. The bypass channel, in some cases, also allows the user to easily stop filling the storage array by unplugging the tubes. In providing an additional outlet of low hydrodynamic resistance, the bypass channel may serve to dampen the abrupt pressure change, and thus prevent the array of droplets from being disturbed.

Once the flow of droplets into the pots array is stopped, droplets were trapped in the pots. Not wishing to be bound by any theory, once the droplets were trapped in the pots, they may have achieved their minimal energy shape, a sphere. Any deviations from a spherical shape may create an increase in surface area, and thus free energy. Droplets are thereby prevented from entering the constrictions between different pots. FIG. 4 is an optical micrograph of droplets trapped in pots as described in this example. In this set of experiments, the ratio of the diameters of the pots to constrictions had to be greater than ~2:1. In cases where the constrictions were larger than this, droplets were able to squeeze through and did not remain in single pots over the course of the experiment.

The device and method of droplet storage described in this example was proven to be stable and robust. The device was moved, heated in an incubator and on a hot plate, and imaged without affecting the position of droplets. The large surface area-to-volume of the droplets, as well as the permeability of PDMS to gases, made this device especially amenable to cell culture under specific environmental conditions. The device described in this example also easily interfaced with standard equipment in biological facilities: the device can be adapted to fit into a microarray scanner or onto the stage of an inverted microscope. Microscopes equipped with an automated stage enable thousands of droplets to be imaged over time. After the experiment, droplets were easily recovered from the storage device by connecting tubing and injecting oil into the device.

Example 2

To demonstrate the capability to perform time-lapse measurements using a device according to one embodiment of the invention, growth rates in a population of single yeast cells were monitored. Yeast cell cultures (*S. cerevisiae*, MATa s288c) were inoculated from a single colony and grown for 6 hours in YPD media at 30° C. A 10 μL aliquot of this stock culture was diluted in 10 mL of YPD and cultured overnight to a density of OD600~0.02-0.06 or 0.2-0.6 (1 mm path length, NanoDrop ND-1000, Wilmington, Del.). Cells are washed twice by centrifugation, resuspended in fresh YPD, and then encapsulated.

Yeast cells were encapsulated in droplets of water-in-fluorocarbon emulsion, and immobilized in pots on a device. To achieve the encapsulation, the cell suspension was loaded into 1 mL plastic syringes (BD) fitted with a 27¾ gauge needle (Luer-lock, 27¾ gauge). PE-20 tubing was inserted onto the needle, and the tubing was plugged into the excised hole on the PDMS device. To encapsulate single cells in droplets, cell suspensions were flowed together with oil (Fluorinert (FC-40 Sigma) containing 1.8% fluorinated surfactant (Holtze et al, in preparation) using flow-focusing geometry 14 to generate monodisperse droplets of a water-in-oil emulsion. Syringe pumps (New Era Pump Systems Inc., Farmingdale, N.Y.) were used to control flow rates: 100 µl/hr for the aqueous phase and 300 µl/hr for the oil phase results in droplets of ~20 µm diameter.

Figure 5A:
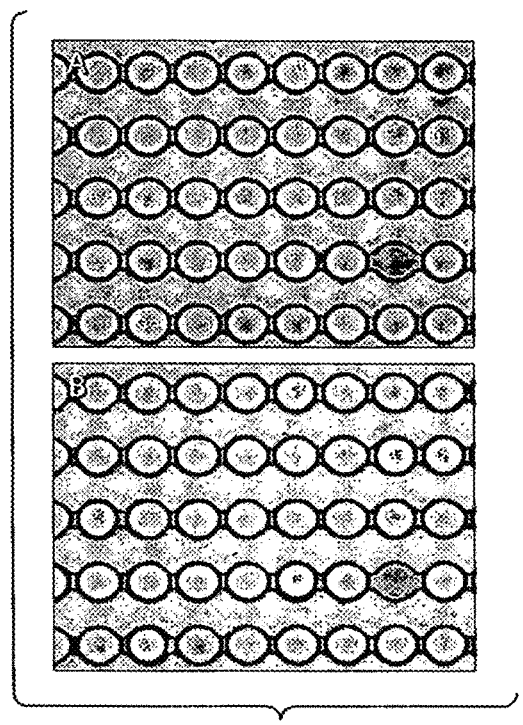
FIGS. 5A-5B include (a) an optical micrograph of an article according to one embodiment of the invention during an example experiment and (b) a plot of generation time versus the number of initially encapsulated cells during an example experiment.
Figure 5B:
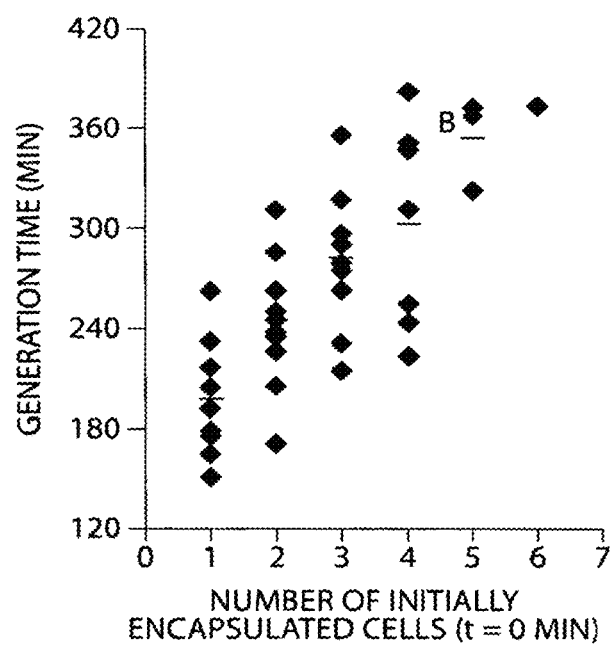
Figure 7A:
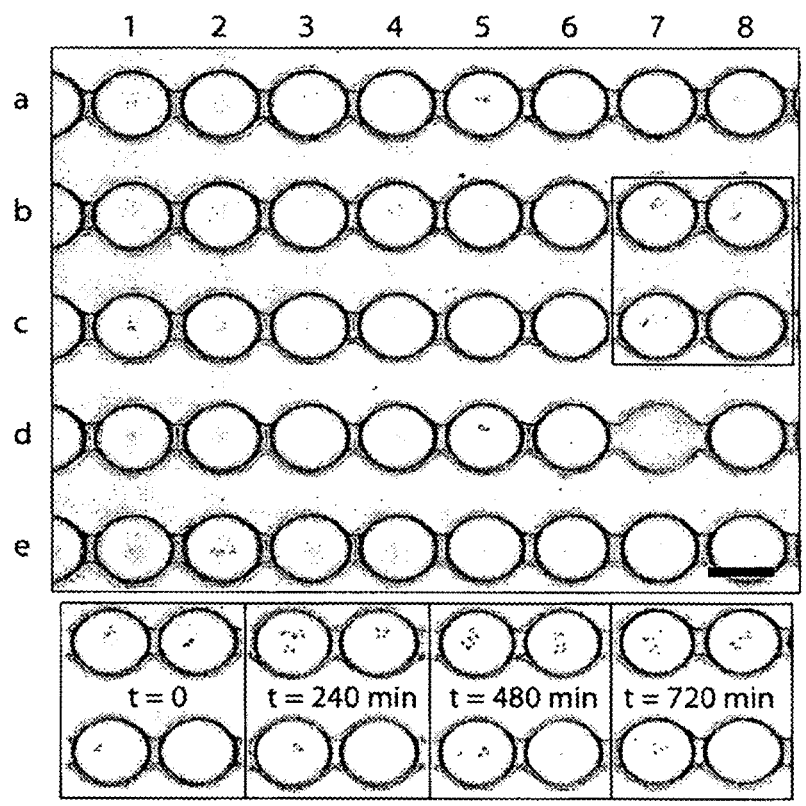
FIGS. 7A-7B include (a) an optical micrograph of an article according to one embodiment of the invention during an example experiment and (b) a plot of the number of cells as a function of time during an example experiment.
Figure 7B:
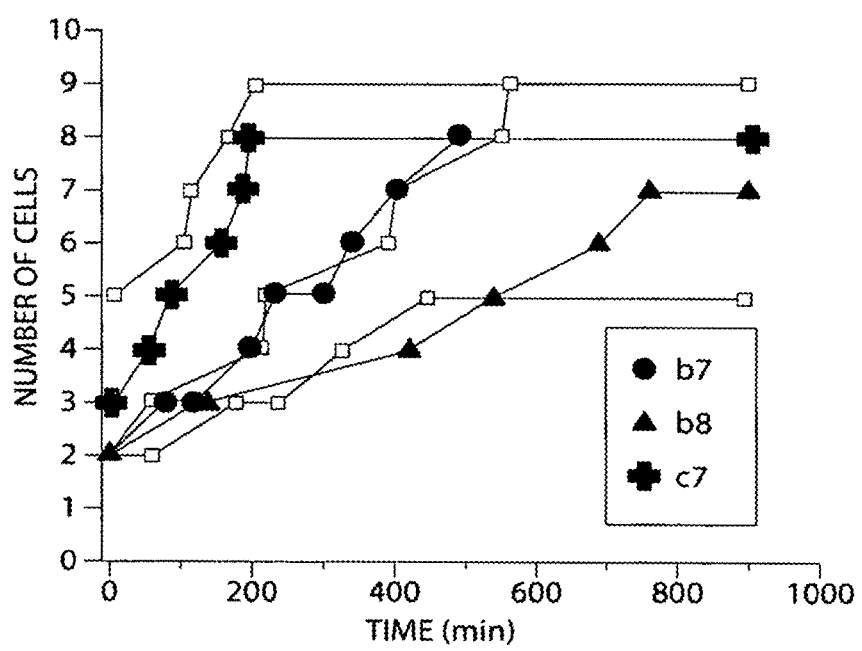

Once the cells were encapsulated and the droplets were arranged in pots, the device containing the cells was incubated overnight. An array of 160 pots was monitored over 15 hours, with images acquired every 10 minutes. FIG. 5 illustrates a typical encapsulation experiment. In this example, 151 pots were filled with droplets, and 71 of those contained one or more cells. The presence of multiple cells in a droplet did not pose a problem, as individual droplets were tracked from time zero, and thus droplets that contained single cells were selected for analysis. The total number of cells increased from 158 to 444. In seven droplets no cell division was observed over the total 15-hour time period. FIG. 7A is an optical micrograph showing the increase in number of cells in one experiment. FIG. 7B includes a plot of the cell growth in pots B7, B8, and C7 during the experiment shown in FIG. 7A.

Plotting the total number of cells as function of time yielded typical sigmoidal growth curves observed for bulk cell culture. The initial generation time was lower than typical values for bulk growth. Not wishing to be bound by any theory, this may have been due to the high "cell density" in the droplets. The volume per cell of a single cell in a droplet of 40 micron diameter is equivalent to 108 cells per mL, which is near the density of a saturated culture of yeast cells. The observed delay in initial division may also have been due to the lag phase.

The generation time for encapsulated cells as function of initially encapsulated cell number was also examined. The doubling time increased with increasing cell number. Although mean values of doubling time clearly followed the trend mentioned above, the doubling time varied significantly among cells in droplets, even when identical numbers of cells are encapsulated. This demonstrates the heterogeneity of cell behavior at the single cell level, one major factor asynchronization of the cell cycle in individual cells.

During timecourse experiments, it was observed that droplets shrank in volume. This may have been due to absorbance of water by the PDMS. To prevent droplets from shrinking, the PDMS could be, in some cases, saturated with media. This was accomplished by filling the water channel reservoir. A cover glass was placed on top of the channels to further prevent droplet shrinkage. When this scheme was adopted, the volumes of droplets containing cell media (YPD) remained constant. In an array of droplets containing cells, however, the volume of empty droplets increased, whereas droplets containing cells shrank as a function of time. Interestingly, the final volume of the droplets decreases with the number of initially encapsulated cells.

Not wishing to be bound by any theory, the following explanation may explain the behavior: cells inside droplets may have consumed more molecules than they excreted, and thus, the osmolarity of the media inside the droplet may have been lowered. This may have led to an osmotic pressure difference which may have forced water from droplets containing cells into empty droplets. This could be a very interesting tool to easily observe metabolic rates at the single cell level.

Example 3

Figure 8A:
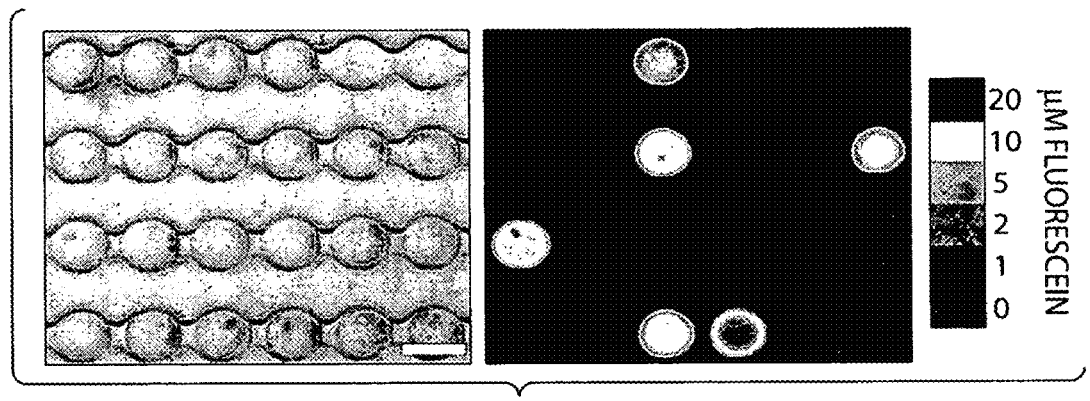
FIGS. 8A-8C include (a) an optical micrograph and color map gradient from an example experiment, (b) a plot of relative fluorescence as a function of time in an example experiment, and (c) a plot of the number of droplets with various rates of fluorescein production in an example experiment.
Figure 8B:
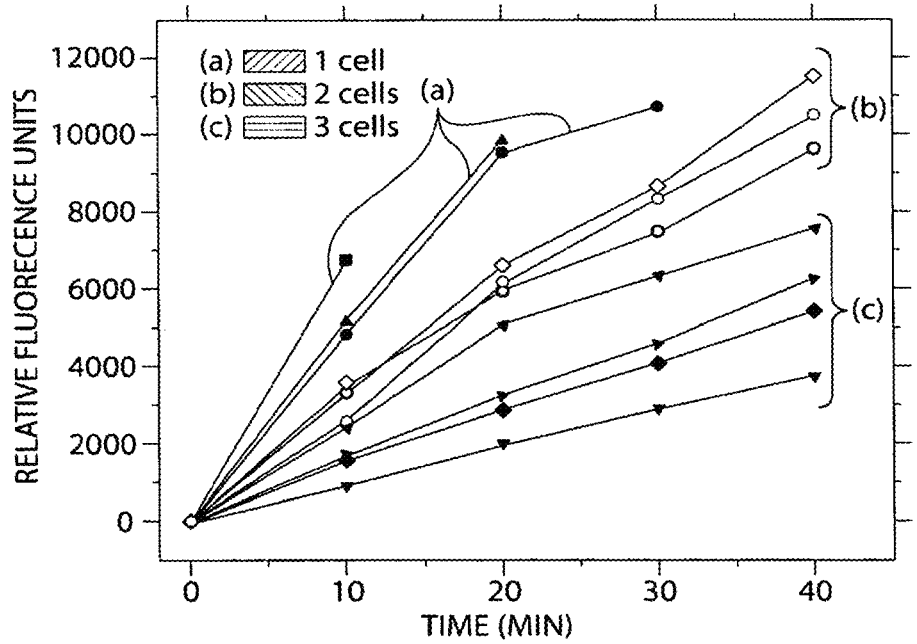
Figure 8C:
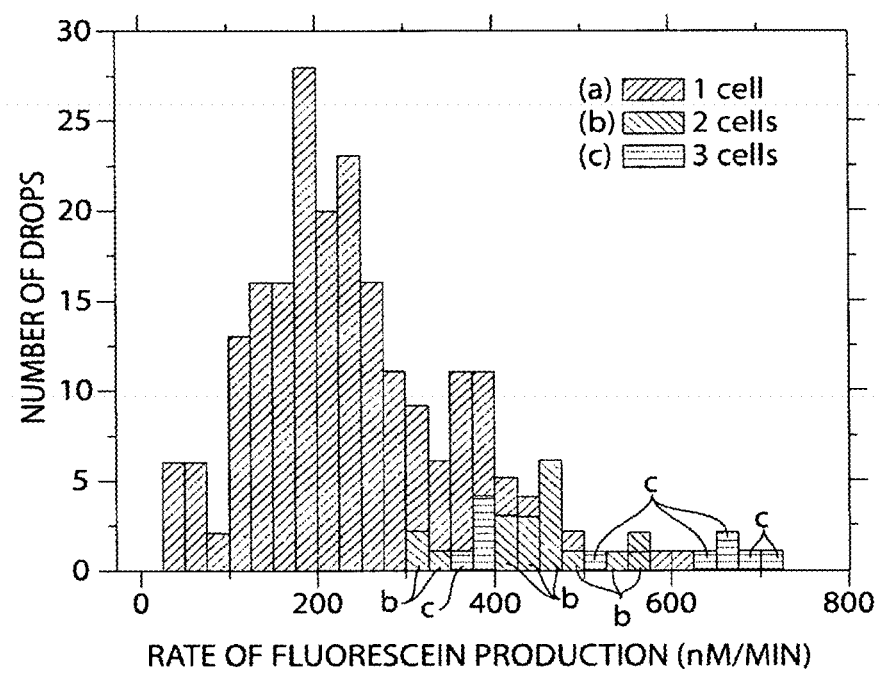

Droplets are helpful in studying populations of single cells and compounds they secrete as high concentrations of molecules are rapidly attained in such small droplet volumes. Secreted enzymes have been used as reporters for gene expression, both for high-throughput screening as well as for fundamental studies of enzyme kinetics and gene expression. To demonstrate the utility of droplets as microvessels for secreted enzyme detection at the single cell level, single cells were encapsulated producing beta-galactosidase, and monitored production of fluorescein (FIG. 8A) as the enzyme cleaved its fluorogenic substrate, fluorescein-di-beta-D-galactopyranoside (FDG). FIG. 8A includes a Brightfield image and color map gradient of a fluorescence image at time ¼ 45 min. For cells in the picoliter-volume droplets of a Dropspots array, the signal was detected after minutes. Slope analysis in the linear regime of the enzyme progress curves showed that reaction rates depend on the number of cells per droplet, but vary even for droplets containing the same number of cells, reflecting heterogeneity in gene expression in a population of isogenic cells (FIGS. 8B-C). FIG. 8B includes plots for 9 individual representative droplets containing 1, 2, and 3 cells. Reaction rates for 265 droplets containing cells were quantified by slope analysis in the linear regime, and displayed as a function of number of cells per droplet in the histogram shown in FIG. 8C. A total of over 2000 droplets were analyzed, but data is displayed only for droplets that contained cells. The scale bar in FIG. 8C represents 40 mm. Previous studies of enzyme kinetics at the single cell level have been limited by their dynamic range, as detectable levels of enzyme must first accumulate in the encapsulation volume before analysis can begin.

Example 4

Lipid vesicles provide a model system to study membranes and lipid bilayers. To avoid the effects of substrate interactions, free-floating lipid vesicles are desirable for use in studies of lateral membrane organization. They are also well-suited for use as biocompatible vessels for encapsulation and targeted drug delivery. In order to stabilize vesicles for studying their physical properties such as lateral organization by confocal microscopy, or permeability, extraneous compounds that may alter lipid bilayer properties (e.g., sugars) are added to the buffer to gravitationally stabilize the vesicles. The Dropspots device may be used to trap lipid vesicles without the addition of exogeneous substances. Permeability can be studied by monitoring by microscopy the volume changes in vesicles in response to osmotic changes. An immobilized array of vesicles would also enable the study of dynamic behavior of encapsulated contents, where the lipid vesicle serves as an in vitro compartment.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device for storing cells comprising:
    a plurality of storage channels arranged in series wherein each storage channel comprises one or more pots each comprising a constriction having a smallest cross-sectional dimension perpendicular to fluid flow through the plurality of storage channels that is smaller than an average cross-sectional dimension of a single cell; and
    one or more bypass channels bypassing one or more of the plurality of storage channels,
    wherein each pot has no more than two constrictions and is in direct fluid communication with no more than two other pots.

2. The device of claim 1, wherein the volumes of the one or more pots are about 10 nanoliters.

3. The device of claim 1, further comprising:
    a gas-permeable membrane that separates the contents of the one or more pots from a controlled environment.

4. The device of claim 1, further comprising:
    a gas-permeable membrane that separates the contents of the one or more pots from ambient atmosphere.

5. The device of claim 1, further comprising a thermal cycler operably associated with the one or more pots.

6. The device of claim 1, wherein each pot is connected to exactly two constrictions.

* * * * *